United States Patent
Geiselmann et al.

(10) Patent No.: US 9,816,123 B2
(45) Date of Patent: Nov. 14, 2017

(54) METHOD FOR PRODUCING METABOLITES, PEPTIDES AND RECOMBINANT PROTEINS

(71) Applicants: Inria Institut National De Recherche En Informatique Et En Automatique, Le Chesnay (FR); Universite Joseph Fourier—Grenoble 1, St. Martin d'Héres (FR)

(72) Inventors: Johannes Geiselmann, La Tronche (FR); Hidde De Jong, Grenoble (FR); Delphine Ropers, Grenoble (FR); Jérôme Izard, Saint Ismier (FR)

(73) Assignees: Inria Institut National De Racherche En Informatiq, Le Chesney (FR); Universite Joseph Fourier-Grenoble 1, Martin d'Heres (FR)

( * ) Notice: Subject to any disclaimer, the term of this patent is extended or adjusted under 35 U.S.C. 154(b) by 57 days.

(21) Appl. No.: 15/022,284

(22) PCT Filed: Sep. 16, 2014

(86) PCT No.: PCT/EP2014/069719
§ 371 (c)(1),
(2) Date: Mar. 16, 2016

(87) PCT Pub. No.: WO2015/036622
PCT Pub. Date: Mar. 19, 2015

(65) Prior Publication Data
US 2016/0222428 A1   Aug. 4, 2016

(30) Foreign Application Priority Data
Sep. 16, 2013   (EP) .................................. 13306266

(51) Int. Cl.
*C12P 7/20* (2006.01)
*C12P 21/00* (2006.01)
*C12P 21/02* (2006.01)
*C12N 9/12* (2006.01)
*C12N 15/72* (2006.01)
*C12N 15/70* (2006.01)

(52) U.S. Cl.
CPC ............ *C12P 21/00* (2013.01); *C12N 9/1247* (2013.01); *C12N 15/70* (2013.01); *C12N 15/72* (2013.01); *C12P 7/20* (2013.01); *C12P 21/02* (2013.01); *C12Y 207/07006* (2013.01)

(58) Field of Classification Search
CPC .............................................. C12Y 207/07006
See application file for complete search history.

(56) References Cited

FOREIGN PATENT DOCUMENTS

WO   2006/055292 A2   5/2006
WO   2007/071959 A1   6/2007

OTHER PUBLICATIONS

Fukuda et al. 1983; Mechanism of the rifampicin induction of RNA polymerase b and b' subunit synthesis in *E. coli*. J. Biol. Chem. 258(4) 2720-2727.*
Meek et al. 1986; Direct evidence for the autogenous regulation of the *Escherichia coli* genes of rpoBC. Mol. Gen Genet 202: 500-508.*
Dykxhoorn, DM, et al., "Synthesis of the Beta and Beta' Subunits of *Escherichia coli* RNA Polymerase is Autogenously Regulated in Vivo by Both Transcriptional and Translational Mechanisms", Molecular Microbiology, Feb. 1, 1996, pp. 483-493, vol. 9, No. 3.
Rowe, Duncan, et al., "The Quiescent-Cell Expression System for Protein Synthesis in *Escherichia coli*", Applied and Environmental Microbiology, Jun. 1, 1999, pp. 2710-2715, vol. 65, No. 6.
Chaitali, Ghosh, et al., "An Inverse Metabolic Engineering Approach for the Design of an Improved Host Platform for Over-Expression of Recombinant Proteins in *Escherichia coli*," Microbial Cell Factories, Jul. 3, 2012, p. 1-9, vol. 11, No. 1.
Sonderegger, Marco, et al., "Selection of Quiescent *Escherichia coli* with High Metabolic Activity", Metabolic Engineering, Jan. 1, 2005, pp. 4-9, vol. 7, No. 1.
Mukherjee, K. J., et al., Studies of Single-Chain Antibody Expression in Quiescent *Escherichia coli*:, Applied and Environmental Microbiology, May 1, 2004, pp. 3005-3012, vol. 70, No. 5.
Milias-Argeitis, Andres, et al., "In Silico Feedback for in Vivo Regulation of a Gene Expression Circuit", Nature Biotechnology, Nov. 6, 2011, vol. 29, No. 12, pp. 1114-1116.
Meighen, Edward, "Molecular Biology of Bacterial Bioluminescene", Microbiological Reviews, Mar. 1991, vol. 55, No. 1, pp. 123-142.
Liang, Quanfeng, et al., "Construction of Stress-Induced Metabolic Pathway from Glucose to 1,3-propanediol in *Escherichia coli*", Applied Microbiology and Biotechnology, Aug. 28, 2010, vol. 89, pp. 57-62.
Liang, S.T., et al., "Activities of Constitutive Promoters in *Escherichia coli*", Journal of Molecular Biology, 1999, vol. 292, pp. 19-37.
Zaslaver, Alon, et al., "A Comprehensive Library of Fluorescent Transcriptional Reporters for *Escherichia coli*", Nature Methods, Aug. 2006, vol. 3, No. 8, pp. 623-628.
Terpe, Kay, "Overview of Bacterial Expression Systems for Heterologous Protein Production: From Molecular and Biochemical Fundamentals to Commercial Systems", Applied Microbiology and Biotechnology, Jun. 22, 2006, vol. 72, pp. 211-222.
Pitera, Douglas, et al., "Balancing a Heterologus Mevalonate Pathway for Improved Isoprenoid Production in *Escherichia coli*", Metabolic Engineering, Nov. 23, 2006, vol. 9, pp. 193-207.
Glick, Bernard, "Metabolic Load and Heterologous Gene Expression", Biotechnology Advances, 1995, vol. 13, No. 2, pp. 247-261.

(Continued)

*Primary Examiner* — Karen Cochrane Carlson
(74) *Attorney, Agent, or Firm* — Maynard, Cooper & Gale, P.C.; Brian Sattizahn

(57) ABSTRACT

The present invention relates to a method for producing a molecule of interest in bacteria which is based on a reversible growth arrest of the bacteria at the cellular growth global control system level, thus allowing an improved yield of production of said molecule of interest.

13 Claims, 1 Drawing Sheet

(56) References Cited

OTHER PUBLICATIONS

Levskaya, Anselm, et al., "Engineering *Escherichia coli* to See Light", Nature Publishing Group, Nov. 24, 2005, vol. 438, pp. 441-442.

Kuhlman, Thomas, et al., "Combinatorial Transcriptional Control of the Lactose Operon of *Escherichia coli*", Proceedings of the National Academy of Sciences, Apr. 3, 2007, vol. 1543, No. 14, pp. 6043-6048.

Chotani, Gopal, et al., "The Commercial Production of Chemicals Using Pathway Engineering", Biochimica et Biophysica Acta, Sep. 28, 2000, pp. 434-455.

Santos, Christine, et al., "Combinatorial Engineering of Microbes for Optimizing Cellular Phenotype," Current Opinion in Chemical Biology, 2008, vol. 12, pp. 168-176.

Cambray, Guillaume, et al., "Measurement and Modeling of Intrinsic Transcription Terminators", Nucleic Acids Research, Mar. 19, 2013, vol. 41, No. 9, pp. 5139-5148.

Lutz, Rolf, et al., "Independent and Tight Regulation of Transcriptional Units in *Escherichia coli* Via the LacR/O, the TetR/O and AraC/I1-I2 Regulatory Elements", Nucleic Acids Research, Jan. 7, 1997, vol. 25, No. 6, pp. 1203-1210.

Borukhov, Sergei, et al., "RNA Polymerase: The Vehicle of Transcription", Trends in Microbiology, Feb. 14, 2008, vol. 16, No. 3, pp. 126-134.

Berthoumieux, Sara, et al., "Shared Control of Gene Expression in Bacteria by Transcription Factors and Global Physiology of the Cell", Molecular Systems Biology, 2013, vol. 9, Article 634, pp. 1-11.

Baek, Kyung-Hwa, et al., "Monitoring of Microbial Diversity and Activity During Bioremediation of Crude Oil-Contaminated Soil with Different Treatments", Journal of Microbiology and Biotechnology, Sep. 26, 2006, vol. 17, No. 1, pp. 67-73.

Alper, Hal, et al., "Global Transcription Machinery Engineering: A New Approach for Improving Cellular Phenotype", Metabolic Engineering, Jan. 8, 2007, vol. 9, pp. 258-267.

Cold Spring Harbor Protocols (doi:10.1101/pdb.rec12295) 2010, 1 page.

\* cited by examiner

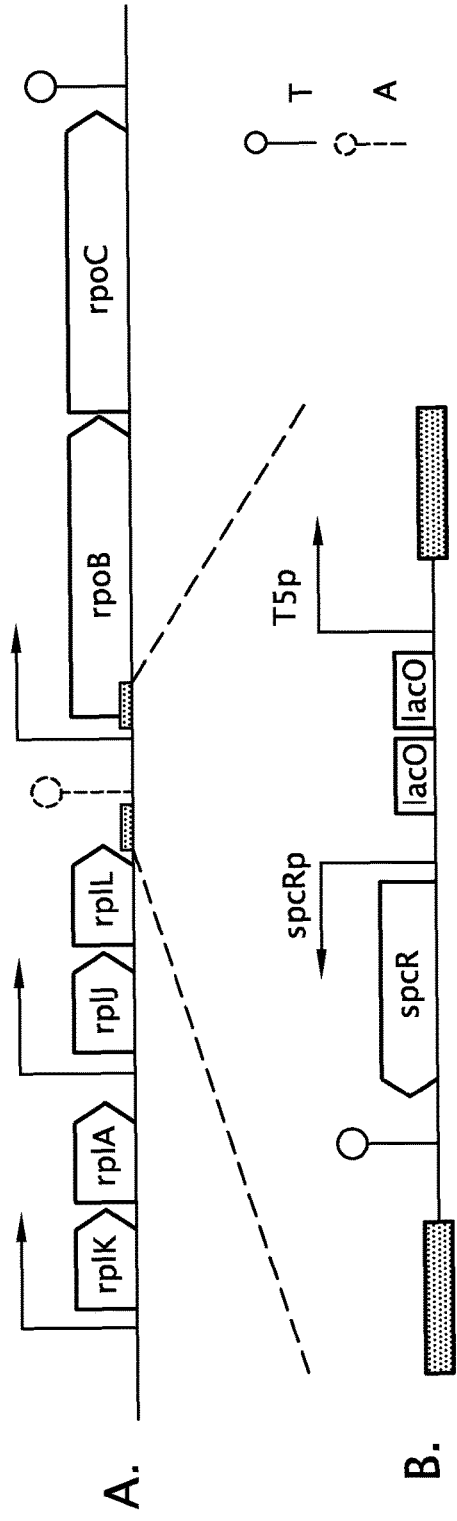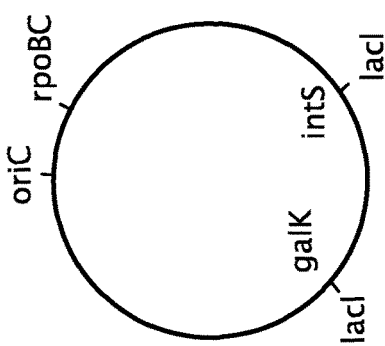
FIG.1
FIG.2

SEQUENCE LISTING

```
<160> NUMBER OF SEQ ID NOS: 7

<210> SEQ ID NO 1
<211> LENGTH: 4029
<212> TYPE: DNA
<213> ORGANISM: Escherichia coli

<400> SEQUENCE: 1
atggtttact cctataccga gaaaaaacgt attcgtaagg attttggtaa acgtccacaa      60
gttctggatg taccttatct cctttctatc cagcttgact cgtttcagaa atttatcgag     120
caagatcctg aagggcagta tggtctggaa gctgctttcc gttccgtatt cccgattcag     180
agctacagcg gtaattccga gctgcaatac gtcagctacc gccttggcga accggtgttt     240
gacgtccagg aatgtcaaat ccgtggcgtg acctattccg caccgctgcg cgttaaactg     300
cgtctggtga tctatgagcg cgaagcgccg gaaggcaccg taaaagacat taaagaacaa     360
gaagtctaca tgggcgaaat tccgctcatg acagacaacg gtacctttgt tatcaacggt     420
actgagcgtg ttatcgtttc ccagctgcac cgtagtccgg gcgtcttctt tgactccgac     480
aaaggtaaaa cccactcttc gggtaaagtg ctgtataacg cgcgtatcat cccttaccgt     540
ggttcctggc tggacttcga attcgatccg aaggacaacc tgttcgtacg tatcgaccgt     600
cgccgtaaac tgcctgcgac catcattctg cgcgccctga actacaccac agagcagatc     660
ctcgacctgt tctttgaaaa agttatcttt gaaatccgtg ataacaagct gcagatggaa     720
ctggtgccgg aacgcctgcg tggtgaaacc gcatcttttg acatcgaagc taacggtaaa     780
gtgtacgtag aaaaaggccg ccgtatcact gcgcgccaca ttcgccagct ggaaaaagac     840
gacgtcaaac tgatcgaagt cccggttgag tacatcgcag gtaaagtggt tgctaaagac     900
tatattgatg agtctaccgg cgagctgatc tgcgcagcga acatggagct gagcctggat     960
ctgctggcta agctgagcca gtctggtcac aagcgtatcg aaacgctgtt caccaacgat    1020
ctggatcacg gcccatatat ctctgaaacc ttacgtgtcg acccaactaa cgaccgtctg    1080
agcgcactgg tagaaatcta ccgcatgatg cgccctggcg agccgccgac tcgtgaagca    1140
gctgaaagcc tgttcgagaa cctgttcttc tccgaagacc gttatgactt gtctgcggtt    1200
ggtcgtatga agttcaaccg ttctctgctg cgcgaagaaa tcgaaggttc cggtatcctg    1260
```

```
agcaaagacg acatcattga tgttatgaaa aagctcatcg atatccgtaa cggtaaaggc   1320
gaagtcgatg atatcgacca cctcggcaac cgtcgtatcc gttccgttgg cgaaatggcg   1380
gaaaaccagt tccgcgttgg cctggtacgt gtagagcgtg cggtgaaaga gcgtctgtct   1440
ctgggcgatc tggataccct gatgccacag gatatgatca acgccaagcc gatttccgca   1500
gcagtgaaag agttcttcgg ttccagccag ctgtctcagt ttatggacca gaacaacccg   1560
ctgtctgaga ttacgcacaa acgtcgtatc tccgcactcg gcccaggcgg tctgacccgt   1620
gaacgtgcag gcttcgaagt tcgagacgta caccccgactc actacggtcg cgtatgtcca   1680
atcgaaaccc ctgaaggtcc gaacatcggt ctgatcaact ctctgtccgt gtacgcacag   1740
actaacgaat acggcttcct tgagactccg tatcgtaaag tgaccgacgg tgttgtaact   1800
gacgaaattc actacctgtc tgctatcgaa aaggcaact acgttatcgc ccaggcgaac   1860
tccaacttgg atgaagaagg ccacttcgta gaagacctgg taacttgccg tagcaaaggc   1920
gaatccagct tgttcagccg cgaccaggtt gactacatgg acgtatccac ccagcaggtg   1980
gtatccgtcg gtgcgtccct gatcccgttc ctggaacacg atgacgccaa ccgtgcattg   2040
atgggtgcga acatgcaacg tcaggccgtt ccgactctgc gcgctgataa gccgctggtt   2100
ggtactggta tggaacgtgc tgttgccgtt gactccggtg taactgcggt agctaaacgt   2160
ggtggtgtcg ttcagtacgt ggatgcttcc cgtatcgtta tcaaagttaa cgaagacgag   2220
atgtatccgg gtgaagcagg tatcgacatc tacaacctga ccaaatacac ccgttctaac   2280
cagaacacct gtatcaacca gatgccgtgt gtgtctctgg gtgaaccggt gaacgtggc   2340 gacgtgctgg cagacggtcc gtccaccgac ctcggtgaac tggcgcttgg tcagaacatg   2400
cgcgtagcgt tcatgccgtg gaatggttac aacttcgaag actccatcct cgtatccgag   2460
cgtgttgttc aggaagaccg tttcaccacc atccacattc aggaactggc gtgtgtgtcc   2520
cgtgacacca agctgggtcc ggaagagatc accgctgaca tcccgaacgt gggtgaagct   2580
gcgctctcca aactgatga atccggtatc gtttacattg gtgcggaagt gaccggtggc   2640
gacattctgg ttggtaaggt aacgccgaaa ggtgaaactc agctgacccc agaagaaaaa   2700
ctgctgcgtg cgatcttcgg tgagaaagcc tctgacgtta aagactcttc tctgcgcgta   2760
ccaaacggtg tatccggtac ggttatcgac gttcaggtct ttactcgcga tggcgtagaa   2820
aaagacaaac gtcgcgctgga aatcgaagaa atgcagctca acaggcgaa gaaagacctg   2880 tctgaagaac tgcagatcct cgaagcgggt ctgttcagcc gtatccgtgc tgtgctggta   2940
gccggtggcg ttgaagctga aagctcgac aaactgccgc gcgatcgctg gctgagctg   3000 ggcctgacag acgaagagaa acaaaatcag ctggaacagc tggctgagca gtatgacgaa   3060
ctgaaacacg agttcgagaa gaaactcgaa gcgaaacgcc gcaaaatcac ccagggcgac   3120
gatctggcac cgggcgtgct gaagattgtt aaggtatatc tggcggttaa acgccgtatc   3180
cagcctggtg acaagatggc aggtcgtcac ggtaacaagg gtgtaatttc taagatcaac   3240
ccgatcgaag atatgcctta cgatgaaaac ggtacgccgg tagacatcgt actgaacccg   3300
ctgggcgtac cgtctcgtat gaacatcggt cagatcctcg aaacccacct gggtatggct   3360 gcgaaggta tcggcgacaa gatcaacgcc atgctgaaac agcagcaaga agtcgcgaaa   3420
ctgcgcgaat tcatccagcg tgcgtacgat ctgggcgctg acgttcgtca gaaagttgac   3480
ctgagtacct tcagcgatga agaagttatg cgtctggctg aaaacctgcg caaaggtatg   3540
ccaatcgcaa cgccggtgtt cgacggtgcg aaagaagcag aaattaaaga gctgctgaaa   3600
cttggcgacc tgccgacttc cggtcagatc cgcctgtacg atggtcgcac tggtgaacag   3660
```

| | |
|---|---|
| ttcgagcgtc cggtaaccgt tggttacatg tacatgctga aactgaacca cctggtcgac | 3720 |
| gacaagatgc acgcgcgttc caccggttct tacagcctgg ttactcagca gccgctgggt | 3780 |
| ggtaaggcac agttcggtgg tcagcgtttc ggggagatgg aagtgtgggc gctggaagca | 3840 |
| tacggcgcag catacaccct gcaggaaatg ctcaccgtta agtctgatga cgtgaacggt | 3900 |
| cgtaccaaga tgtataaaaa catcgtggac ggcaaccatc agatggagcc gggcatgcca | 3960 |
| gaatccttca acgtattgtt gaaagagatt cgttcgctgg gtatcaacat cgaactggaa | 4020 |
| gacgagtaa | 4029 |

<210> SEQ ID NO 2
<211> LENGTH: 4224
<212> TYPE: DNA
<213> ORGANISM: Escherichia coli

<400> SEQUENCE: 2

| | |
|---|---|
| gtgaaagatt tattaaagtt tctgaaagcg cagactaaaa ccgaagagtt tgatgcgatc | 60 |
| aaaattgctc tggcttcgcc agacatgatc cgttcatggt ctttcggtga agttaaaaag | 120 |
| ccggaaacca tcaactaccg tacgttcaaa ccagaacgtg acggccttt ctgcgcccgt | 180 |
| atctttgggc cggtaaaaga ttacgagtgc ctgtgcggta agtacaagcg cctgaaacac | 240 |
| cgtggcgtca tctgtgagaa gtgcggcgtt gaagtgaccc agactaaagt acgccgtgag | 300 |
| cgtatgggcc acatcgaact ggcttccccg actgcgcaca tctggttcct gaaatcgctg | 360 |
| ccgtcccgta tcggtctgct gctcgatatg ccgctgcgcg atatcgaacg cgtactgtac | 420 |
| tttgaatcct atgtggttat cgaaggcggt atgaccaacc tggaacgtca gcagatcctg | 480 |
| actgaagagc agtatctgga cgcgctggaa gagttcggtg acgaattcga cgcgaagatg | 540 |
| ggggcggaag caatccaggc tctgctgaag agcatggatc tggagcaaga gtgcgaacag | 600 |
| ctgcgtgaag agctgaacga aaccaactcc gaaaccaagc gtaaaaagct gaccaagcgt | 660 |
| atcaaactgc tggaagcgtt cgttcagtct ggtaacaaac cagagtggat gatcctgacc | 720 |
| gttctgccgg tactgccgcc agatctgcgt ccgctggttc cgctggatgg tggtcgtttc | 780 |
| gcgacttctg acctgaacga tctgtatcgt cgcgtcatta accgtaacaa ccgtctgaaa | 840 |
| cgtctgctgg atctggctgc gccggacatc atcgtacgta cgaaaaacg tatgctgcag | 900 |
| gaagcggtag acgccctgct ggataacggt cgtcgcggtc gtgcgatcac cggttctaac | 960 |
| aagcgtcctc tgaaatcttt ggccgacatg atcaaaggta acagggtcg tttccgtcag | 1020 |
| aacctgctcg gtaagcgtgt tgactactcc ggtcgttctg taatcaccgt aggtccatac | 1080 |
| ctgcgtctgc atcagtgcgg tctgccgaag aaaatggcac tggagctgtt caaaccgttc | 1140 |
| atctacggca gctggaact gcgtggtctt gctaccacca ttaaagctgc gaagaaaatg | 1200 |
| gttgagcgcg aagaagctgt cgtttgggat atcctggacg aagttatccg cgaacacccg | 1260 |
| gtactgctga accgtgcacc gactctgcac cgtctgggta tccaggcatt tgaaccggta | 1320 |
| ctgatcgaag gtaaagctat ccagctgcac ccgctggttt gtcggcata taacgccgac | 1380 |
| ttcgatggtg accagatggc tgttcacgta ccgctgacgc tggaagccca gctggaagcg | 1440 |
| cgtgcgctga tgatgtctac caacaacatc ctgtccccgg cgaacggcga accaatcatc | 1500 |
| gttccgtctc aggacgttgt actgggtctg tactacatga cccgtgactg tgttaacgcc | 1560 |
| aaaggcgaag gcatggtgct gactggcccg aaagaagcag aacgtctgta tcgctctggt | 1620 |
| ctggcttctc tgcatgcgcg cgttaaagtg cgtatcaccg agtatgaaaa agatgctaac | 1680 |

```
ggtgaattag tagcgaaaac cagcctgaaa gacacgactg ttggccgtgc cattctgtgg    1740
atgattgtac cgaaaggtct gccttactcc atcgtcaacc aggcgctggg taaaaaagca    1800
atctccaaaa tgctgaacac ctgctaccgc attctcggtc tgaaaccgac cgttattttt    1860
gcggaccaga tcatgtacac cggcttcgcc tatgcagcgc gttctggtgc atctgttggt    1920
atcgatgaca tggtcatccc ggagaagaaa cacgaaatca tctccgaggc agaagcagaa    1980
gttgctgaaa ttcaggagca gttccagtct ggtctggtaa ctgcgggcga acgctacaac    2040
aaagttatcg atatctgggc tgcggcgaac gatcgtgtat ccaaagcgat gatggataac    2100
ctgcaaactg aaaccgtgat taaccgtgac ggtcaggaag agaagcaggt ttccttcaac    2160
agcatctaca tgatggccga ctccggtgcg cgtggttctg cggcacagat tcgtcagctt    2220
gctggtatgc gtggtctgat ggcgaagccg atggctcca tcatcgaaac gccaatcacc     2280
gcgaacttcc gtgaaggtct gaacgtactc cagtacttca tctccaccca cggtgctcgt    2340
aaaggtctgg cggataccgc actgaaaact gcgaactccg gttacctgac tcgtcgtctg    2400
gttgacgtgg cgcaggacct ggtggttacc gaagacgatt gtggtaccca tgaaggtatc    2460
atgatgactc cggttatcga gggtggtgac gttaaagagc cgctgcgcga tcgcgtactg    2520
ggtcgtgtaa ctgctgaaga cgttctgaag ccgggtactg ctgatatcct cgttccgcgc    2580
aacacgctgc tgcacgaaca gtggtgtgac ctgctggaag agaactctgt cgacgcggtt    2640
aaagtacgtt ctgttgtatc ttgtgacacc gactttggtg tatgtgcgca ctgctacggt    2700
cgtgacctgg cgcgtggcca catcatcaac aagggtgaag caatcggtgt tatcgcggca    2760
cagtccatcg gtgaaccggg tacacagctg accatgcgta cgttccacat cggtggtgcg    2820
gcatctcgtg cggctgctga atccagcatc caagtgaaaa acaaaggtag catcaagctc    2880
agcaacgtga agtcggttgt gaactccagc ggtaaactgg ttatcacttc ccgtaatact    2940
gaactgaaac tgatcgacga attcggtcgt actaaagaaa gctacaaagt accttacggt    3000
gcggtactgg cgaaaggcga tgcgaacag gttgctggcg gcgaaaccgt tgcaaactgg    3060
gacccgcaca ccatgccggt tatcaccgaa gtaagcggtt ttgtacgctt tactgacatg    3120
atcgacggcc agaccattac gcgtcagacc gacgaactga ccggtctgtc ttcgctggtg    3180
gttctggatt ccgcagaacg taccgcaggt ggtaaagatc tgcgtccggc actgaaaatc    3240
gttgatgctc agggtaacga cgttctgatc ccaggtaccg atatgccagc gcagtacttc    3300
ctgccgggta agcgattgt tcagctggaa gatggcgtac agatcagctc tggtgacacc    3360
ctggcgcgta ttccgcagga atccggcggt accaaggaca tcaccggtgg tctgccgcgc    3420
gttgcggacc tgttcgaagc acgtcgtccg aaagagccgg caatcctggc tgaaatcagc    3480
ggtatcgttt ccttcggtaa agaaaccaaa ggtaaacgtc gtctggttat cacccccggta    3540 gacggtagcg atccgtacga agagatgatt ccgaaatggc gtcagctcaa cgtgttcgaa    3600
ggtgaacgtg tagaacgtgg tgacgtaatt ccgacggtc cggaagcgcc gcacgacatt    3660
ctgcgtctgc gtggtgttca tgctgttact cgttacatcg ttaacgaagt acaggacgta    3720
taccgtctgc agggcgttaa gattaacgat aaacacatcg aagttatcgt tcgtcagatg    3780
ctgcgtaaag ctaccatcgt taacgcgggt agctccgact tcctggaagg cgaacaggtt    3840
gaatactctc gcgtcaagat cgcaaaccgc gaactggaag cgaacggcaa agtgggtgca    3900
acttactccc gcgatctgct gggtatcacc aaagcgtctc tggcaaccga gtccttcatc    3960
tccgcggcat cgttccagga gaccactcgc gtgctgaccg aagcagccgt tgcgggcaaa    4020
cgcgacgaac tgcgcggcct gaaagagaac gttatcgtgg gtcgtctgat cccggcaggt    4080
```

```
accggttacg cgtaccacca ggatcgtatg cgtcgccgtg ctgcgggtga agctccggct    4140
gcaccgcagg tgactgcaga agacgcatct gccagcctgg cagaactgct gaacgcaggt    4200
ctgggcggtt ctgataacga gtaa                                          4224
```

<210> SEQ ID NO 3
<211> LENGTH: 1083
<212> TYPE: DNA
<213> ORGANISM: Escherichia coli

<400> SEQUENCE: 3

```
gtgaaaccag taacgttata cgatgtcgca gagtatgccg gtgtctctta tcagaccgtt      60
tcccgcgtgg tgaaccaggc cagccacgtt tctgcgaaaa cgcgggaaaa agtggaagcg     120
gcgatggcga agctgaatta cattcccaac cgcgtggcac aacaactggc gggcaaacag     180
tcgttgctga ttggcgttgc cacctccagt ctggccctgc acgcgccgtc gcaaattgtc     240
gcggcgatta aatctcgcgc cgatcaactg ggtgccagcg tggtggtgtc gatggtagaa     300
cgaagcggcg tcgaagcctg taaagcggcg gtgcacaatc ttctcgcgca acgcgtcagt     360
gggctgatca ttaactatcc gctggatgac caggatgcca ttgctgtgga agctgcctgc     420
actaatgttc cggcgttatt tcttgatgtc tctgaccaga cacccatcaa cagtattatt     480
ttctcccatg aagacggtac gcgactgggc gtggagcatc tggtcgcatt gggtcaccag     540
caaatcgcgc tgttagcggg cccattaagt tctgtctcgg cgcgtctgcg tctggctggc     600
tggcataaat atctcactcg caatcaaatt cagccgatag cggaacggga aggcgactgg     660
agtgccatgt ccggttttca acaaaccatg caaatgctga atgagggcat cgttcccact     720
gcgatgctgg ttgccaacga tcagatggcg ctgggcgcaa tgcgcgccat taccgagtcc     780
gggctgcgcg ttggtgcgga tatctcggta gtgggatacg acgataccga agacagctca     840
tgttatatcc cgccgttaac caccatcaaa caggattttc gcctgctggg gcaaaccagc     900
gtggaccgct tgctgcaact ctctcagggc caggcggtga agggcaatca gctgttgccc     960
gtctcactgg tgaaaagaaa aaccaccctg gcgcccaata cgcaaaccgc ctctccccgc    1020
gcgttggccg attcattaat gcagctggca cgacaggttt cccgactgga aagcgggcag    1080
tga                                                                 1083
```

<210> SEQ ID NO 4
<211> LENGTH: 1284
<212> TYPE: DNA
<213> ORGANISM: Artificial Sequence
<220> FEATURE:
<223> OTHER INFORMATION: Cloning cassette
<220> FEATURE:
<221> NAME/KEY: misc_feature
<222> LOCATION: (1)..(50)
<223> OTHER INFORMATION: chromosome homology
<220> FEATURE:
<221> NAME/KEY: terminator
<222> LOCATION: (61)..(104)
<223> OTHER INFORMATION: rrnBt1
<220> FEATURE:
<221> NAME/KEY: misc_feature
<222> LOCATION: (117)..(910)
<223> OTHER INFORMATION: spcR selection cassette
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (313)..(313)

<223> OTHER INFORMATION: n is a, c, g, or t
<220> FEATURE:
<221> NAME/KEY: -35_signal
<222> LOCATION: (1135)..(1140)
<220> FEATURE:
<221> NAME/KEY: misc_feature
<222> LOCATION: (1140)..(1157)
<223> OTHER INFORMATION: binding site - lacO1
<220> FEATURE:
<221> NAME/KEY: -10_signal
<222> LOCATION: (1158)..(1163)
<220> FEATURE:
<221> NAME/KEY: misc_feature
<222> LOCATION: (1170)..(1197)
<223> OTHER INFORMATION: binding site - lacO1
<220> FEATURE:
<221> NAME/KEY: RBS
<222> LOCATION: (1207)..(1217)
<220> FEATURE:
<221> NAME/KEY: misc_feature
<222> LOCATION: (1225)..(1284)
<223> OTHER INFORMATION: rpoB homology
<220> FEATURE:
<221> NAME/KEY: misc_feature
<222> LOCATION: (1269)..(1269)
<223> OTHER INFORMATION: n is a, c, g, or t

<400> SEQUENCE: 4

```
cgctgtaagg cgccagtagc gtttcacact gtttgactac tgctgtgcct acgtctcgag      60
ataaaacgaa aggctcagtc gaaagactgg gcctttcgtt ttataattgt tagacattat     120
ttgccggcta ccttggtgat ctcgcccttc acgtagtgga caaattcttc caactgatct     180
gcgcgcgagg ccaagcgatc ttcttcttgt ccaagataag cctgtctagc ttcaagtatg     240
acgggctgat gctgggccgg caggcgctcc attgcccagt cggcagcgac atccttcngg     300
cgcgattttg ccnggttact gcgctgtacc aaatgcggga caacgtaagc actacatttc     360
gctcatcgcc agcccagtcg ggcggcgagt tccatagcgt taaggtttca tttagcgcct     420
caaatagatc ctgttcagga accggatcaa agagttcctc cgccgctgga cctaccaagg     480
caacgctatg ttctcttgct tttgtcagca agatagccag atcaatgtcg atcgtggctg     540
gctcgaagat acctgcaaga atgtcattgc gctgccattc tccaaattgc agttcgcgct     600
tagctggata acgccacggg atgatgtcgt cgtgcacaac aatggtgact tctacagcgc     660
ggagaatctc gctctctcca ggggaagccg aagtttccaa aaggtcgttg atcaaagctc     720
gccgcgttgt ttcgtcaagc cttacggtca ccgtaaccag caaatcaata tcactgtgtg     780
gcttcaggcc gccatccact gcggagccgt acaaatgtac ggccagcaac gtcggttcga     840
gatggcgctc gatgacgcca actacctctg atagttgagt cgatacttcg gcgatcaccg     900
cttccctcat gatgtttaac tttgttttag ggcgactgcc ctgctgcgta acatcgttgc     960
tgctccataa catcaaacat cgacccaggg cgtaacgcgc ttgctgcttg gatgcccgag    1020
gcatagactg taccccaaaa aaacagtcat agcaagccat gaaaaccgcc actgcgccgt    1080
taccaccgct gcgttcggcc aaggttctgg ctcgagaaat cataaaaaat ttatttgctt    1140
tgtgagcgga taacaattac aatagattca attgtaagcg gataacaatt tcacacagaa    1200
ttcattaaag aggagaaatt aactatggtt tactcctata ccgagaaaaa acgtattcgt    1260
aaggatttng gtaaacgtcc acaa                                           1284
```

<210> SEQ ID NO 5
<211> LENGTH: 1277
<212> TYPE: DNA
<213> ORGANISM: Artificial Sequence
<220> FEATURE:

```
<223> OTHER INFORMATION: LacI sequence inserted at galK locus
<220> FEATURE:
<221> NAME/KEY: misc_feature
<222> LOCATION: (1)..(50)
<223> OTHER INFORMATION: homology start galk
<220> FEATURE:
<221> NAME/KEY: -35_signal
<222> LOCATION: (71)..(76)
<220> FEATURE:
<221> NAME/KEY: -10_signal
<222> LOCATION: (96)..(101)
<220> FEATURE:
<221> NAME/KEY: gene
<222> LOCATION: (125)..(1207)
<223> OTHER INFORMATION: lacI
<220> FEATURE:
<221> NAME/KEY: misc_feature
<222> LOCATION: (1230)..(1277)
<223> OTHER INFORMATION: homology end galK

<400> SEQUENCE: 5
gtttgcgcgc agtcagcgat atccattttc gcgaatccgg agtgtaagaa taagctagcg      60
tgacgatgcg ttgacatatc actgtgattc acatataata tgcgaaatca gaagagtatt     120
gctaatgaaa ccagtaacgt tatacgatgt cgcagagtat gccggtgtct cttatcagac     180
cgtttcccgc gtggtgaacc aggccagcca cgtttctgcg aaaacgcggg aaaaagtgga     240
agcggcgatg gcggagctga attacattcc caaccgcgtg gcacaacaac tggcgggcaa     300
acagtcgttg ctgattggcg ttgccacctc cagtctggcc ctgcacgcgc cgtcgcaaat     360
tgtcgcggcg attaaatctc gcgccgatca actgggtgcc agcgtggtgg tgtcgatggt     420
agaacgaagc ggcgtcgaag cctgtaaagc ggcggtgcac aatcttctcg cgcaacgcgt     480
cagtgggctg atcattaact atccgctgga tgaccaggat gccattgctg tggaagctgc     540
ctgcactaat gttccggcgt tatttcttga tgtctctgac cagacaccca tcaacagtat     600
tattttctcc catgaagacg gtacgcgact gggcgtggag catctggtcg cattgggtca     660
ccagcaaatc gcgctgttag cgggcccatt aagttctgtc tcggcgcgtc tgcgtctggc     720
tggctggcat aaatatctca ctcgcaatca aattcagccg atagcggaac gggaaggcga     780
ctggagtgcc atgtccggtt ttcaacaaac catgcaaatg ctgaatgagg gcatcgttcc     840
cactgcgatg ctggttgcca acgatcagat ggcgctgggc gcaatgcgcg ccattaccga     900
gtccgggctg cgcgttggtg cggatatctc ggtagtggga tacgacgata ccgaagacag     960
ctcatgttat atcccgccgt taaccaccat caaacaggat tttcgcctgc tggggcaaac    1020
cagcgtggac cgcttgctgc aactctctca gggccaggcg gtgaagggca atcagctgtt    1080
gcccgtctca ctggtgaaaa gaaaaaccac cctggcgccc aatacgcaaa ccgcctctcc    1140
ccgcgcgttg gccgattcat taatgcagct ggcacgacag gtttcccgac tggaaagcgg    1200
gcagtgactaa aggtgatcag ctagttacgg aagagctggt gcctgccgta cagcaagctg    1260
tcgctgaaca atatgaa                                                   1277

<210> SEQ ID NO 6
<211> LENGTH: 1277
<212> TYPE: DNA
<213> ORGANISM: Artificial Sequence
<220> FEATURE:
<223> OTHER INFORMATION: LacI sequence inserted at intS locus
<220> FEATURE:
<221> NAME/KEY: misc_feature
<222> LOCATION: (1)..(49)
<223> OTHER INFORMATION: homology start of intS
<220> FEATURE:
<221> NAME/KEY: -35_signal
```

```
<222> LOCATION: (71)..(76)
<220> FEATURE:
<221> NAME/KEY: -10_signal
<222> LOCATION: (94)..(99)
<220> FEATURE:
<221> NAME/KEY: gene
<222> LOCATION: (125)..(1207)
<223> OTHER INFORMATION: lacI
<220> FEATURE:
<221> NAME/KEY: misc_feature
<222> LOCATION: (1228)..(1277)
<223> OTHER INFORMATION: homology end of intS

<400> SEQUENCE: 6
```

| | | | | | |
|---|---|---|---|---|---|
| ccgtagattt | acagttcgtc | atggttcgct | tcagatcgtt | gacagccgca | taagctagcg | 60 |
| tgacgatgcg | ttgacatatc | actgtgattc | acatataata | tgcgaaatca | gaagagtatt | 120 |
| gctaatgaaa | ccagtaacgt | tatacgatgt | cgcagagtat | gccggtgtct | cttatcagac | 180 |
| cgtttcccgc | gtggtgaacc | aggccagcca | cgtttctgcg | aaaacgcggg | aaaaagtgga | 240 |
| agcggcgatg | gcggagctga | attacattcc | caaccgcgtg | gcacaacaac | tggcgggcaa | 300 |
| acagtcgttg | ctgattggcg | ttgccacctc | cagtctggcc | ctgcacgcgc | cgtcgcaaat | 360 |
| tgtcgcggcg | attaaatctc | gcgccgatca | actgggtgcc | agcgtggtgg | tgtcgatggt | 420 |
| agaacgaagc | ggcgtcgaag | cctgtaaagc | ggcggtgcac | aatcttctcg | cgcaacgcgt | 480 |
| cagtgggctg | atcattaact | atccgctgga | tgaccaggat | gccattgctg | tggaagctgc | 540 |
| ctgcactaat | gttccggcgt | tatttcttga | tgtctctgac | cagacaccca | tcaacagtat | 600 |
| tattttctcc | catgaagacg | gtacgcgact | gggcgtggag | catctggtcg | cattgggtca | 660 |
| ccagcaaatc | gcgctgttag | cgggcccatt | aagttctgtc | tcggcgcgtc | tgcgtctggc | 720 |
| tggctggcat | aaatatctca | ctcgcaatca | aattcagccg | atagcggaac | gggaaggcga | 780 |
| ctggagtgcc | atgtccggtt | ttcaacaaac | catgcaaatg | ctgaatgagg | gcatcgttcc | 840 |
| cactgcgatg | ctggttgcca | acgatcagat | ggcgctgggc | gcaatgcgcg | ccattaccga | 900 |
| gtccgggctg | cgcgttggtg | cggatatctc | ggtagtggga | tacgacgata | ccgaagacag | 960 |
| ctcatgttat | atcccgccgt | taaccaccat | caaacaggat | tttcgcctgc | tggggcaaac | 1020 |
| cagcgtggac | cgcttgctgc | aactctctca | gggccaggcg | gtgaagggca | atcagctgtt | 1080 |
| gcccgtctca | ctggtgaaaa | gaaaaaccac | cctggcgccc | aatacgcaaa | ccgcctctcc | 1140 |
| ccgcgcgttg | gccgattcat | taatgcagct | ggcacgacag | gtttcccgac | tggaaagcgg | 1200 |
| gcagtgacta | aggtgatcag | ctagttatgg | gcggactggc | ttgatgagaa | ggtggagtga | 1260 |
| gcgaccttaa | caactat | | | | | 1277 |

```
<210> SEQ ID NO 7
<211> LENGTH: 1282
<212> TYPE: DNA
<213> ORGANISM: Artificial Sequence
<220> FEATURE:
<223> OTHER INFORMATION: Cloning cassette
<220> FEATURE:
<221> NAME/KEY: misc_feature
<222> LOCATION: (1)..(50)
<223> OTHER INFORMATION: Chromosome homology
<220> FEATURE:
<221> NAME/KEY: terminator
<222> LOCATION: (61)..(104)
<223> OTHER INFORMATION: rrnBt1
<220> FEATURE:
<221> NAME/KEY: misc_feature
<222> LOCATION: (117)..(908)
<223> OTHER INFORMATION: spcR selection cassette
<220> FEATURE:
```

```
<221> NAME/KEY: -35_signal
<222> LOCATION: (1133)..(1138)
<220> FEATURE:
<221> NAME/KEY: misc_feature
<222> LOCATION: (1138)..(1155)
<223> OTHER INFORMATION: binding site - lacO1
<220> FEATURE:
<221> NAME/KEY: -10_signal
<222> LOCATION: (1156)..(1161)
<220> FEATURE:
<221> NAME/KEY: misc_feature
<222> LOCATION: (1168)..(1195)
<223> OTHER INFORMATION: binding site - lacO1
<220> FEATURE:
<221> NAME/KEY: RBS
<222> LOCATION: (1205)..(1215)
<220> FEATURE:
<221> NAME/KEY: misc_feature
<222> LOCATION: (1223)..(1282)
<223> OTHER INFORMATION: rpoB homology

<400> SEQUENCE: 7
cgctgtaagg cgccagtagc gtttcacact gtttgactac tgctgtgcct acgtctcgag      60
ataaaacgaa aggctcagtc gaaagactgg gcctttcgtt ttataattgt tagacattat     120
ttgccggcta ccttggtgat ctcgcccttc acgtagtgga caaattcttc caactgatct     180
gcgcgcgagg ccaagcgatc ttcttcttgt ccaagataag cctgtctagc ttcaagtatg     240
acgggctgat gctgggccgg caggcgctcc attgccagt cggcagcgac atccttcggc      300
gcgattttgc cggttactgc gctgtaccaa atgcgggaca acgtaagcac tacatttcgc     360
tcatcgccag cccagtcggg cggcgagttc catagcgtta aggtttcatt tagcgcctca     420
aatagatcct gttcaggaac cggatcaaag agttcctccg ccgctggacc taccaaggca     480
acgctatgtt ctcttgcttt tgtcagcaag atagccagat caatgtcgat cgtggctggc     540
tcgaagatac ctgcaagaat gtcattgcgc tgccattctc caaattgcag ttcgcgctta     600
gctggataac gccacgggat gatgtcgtcg tgcacaacaa tggtgacttc tacagcgcgg     660
agaatctcgc tctctccagg ggaagccgaa gtttccaaaa ggtcgttgat caaagctcgc     720
cgcgttgttt cgtcaagcct tacggtcacc gtaaccagca aatcaatatc actgtgtggc     780
ttcaggccgc catccactgc ggagccgtac aaatgtacgg ccagcaacgt cggttcgaga     840
tggcgctcga tgacgccaac tacctctgat agttgagtcg atacttcggc gatcaccgct     900
tccctcatga tgtttaactt tgttttaggg cgactgccct gctgcgtaac atcgttgctg     960
ctccataaca tcaaacatcg acccagggcg taacgcgctt gctgcttgga tgcccgaggc    1020
atagactgta cccaaaaaaa acagtcatag caagccatga aaaccgccac tgcgccgtta    1080
ccaccgctgc gttcggccaa ggttctggct cgagaaatca taaaaatttt atttgctttg    1140
tgagcggata acaattacaa tagattcaat tgtaagcgga taacaatttc acacagaatt    1200
cattaaagag gagaaattaa ctatggttta ctcctatacc gagaaaaaac gtattcgtaa    1260
ggattttggt aaacgtccac aa                                             1282
```

METHOD FOR PRODUCING METABOLITES, PEPTIDES AND RECOMBINANT PROTEINS

FIELD OF THE INVENTION

The present invention concerns biological methods for producing metabolites, peptides and recombinant proteins.

BACKGROUND

One of the key issues in biotechnology is the redesign of microorganisms to optimize the yield of products of interest, such as biofuels, bulk and fine chemicals, or molecules of medical interest. The redesign modifies the metabolic flux distribution such that, ideally, the cells switch from growth, i.e., biomass production, to product synthesis. Industrial biotechnology processes (Chotani et al. (2000) Biochim. Biophys. Acta 1543:434-455) are thus typically split into two stages: (i) while already producing the target compound, a cellular population is grown to a desired size; since most of the available energy is used for biomass formation, the product yield is small; (ii) Cellular growth is shut down to uncouple the production of the target compound from biomass formation (Sonderegger et al. (2005) Metab. Eng. 7:4-9). Growth arrest occurs spontaneously when the cell density reaches a high value, but this situation is characterized by a high morbidity and drastic reduction of metabolic activity: substrate intake fluxes decrease, which severely impairs process productivity.

Maintaining high metabolic activity in the absence of growth is a fundamental problem in biotechnological engineering, since it represents "a phenotype that does not normally exist in the natural environment and which is not straightforward to engineer genetically" (Sonderegger et al. (2005) Metab. Eng. 7:7).

Metabolic engineering has proposed several ways to achieve growth arrest while maintaining metabolic activity. Some are based on targeted genetic modifications that (in) activate specific components of the cell contributing to biomass formation, such as cell-cycle arrest by overexpression of a small RNA regulating cell division (Rowe and Summers (1999) Appl. Environ. Microbiol. 65:2710-2715) or engineering of sigma factors and other global regulatory proteins (Alper et al. (2007) Metab. Eng. 9:258-267; Santos and Stephanopoulos (2008) Curr. Opin. Chem. Biol. 12:168-176). Other strategies rely on shifting the bioreactor to starvation conditions: nitrogen starvation, for example, leads to growth arrest by stopping amino acid synthesis, while phosphate starvation prevents the production of nucleotides.

These genetic or physiological perturbations have a number of drawbacks. For instance, the modification of the expression of selected enzymes may lead to imbalances in the metabolic pathway, resulting in a metabolic burden on the cell detrimental to the production rate of the target compound (Glick (1995) Biotechnol. Adv. 13:247-261; Pitera et al. (2007) Metabol. Eng. 9:193-207). Nitrogen starvation is not possible when the target compound itself has nitrogen atoms (amino acid, polyamides . . . ), while phosphate deprivation causes perturbation on cell energetic processes detrimental to the production (Baek et al. (2007) J. Microbiol. Biotechnol. 17:244-252).

There is therefore still a need for improved biological methods of production of metabolites, peptides or recombinant proteins that do not present these drawbacks and that preferably allow increasing the yield of production of the molecule of interest.

SUMMARY OF THE INVENTION

The present invention relates to a method for producing a molecule of interest in bacteria that is based on a reversible growth arrest of the bacteria at the level of the global cellular growth-control system, thus allowing an improved yield of production of said molecule of interest.

The present invention arises from the unexpected finding by the inventors that, instead of interfering with the functioning of specific pathways, it is more efficient to directly act upon the global regulatory mechanisms controlling cellular dynamic, in particular upon the gene expression machinery (GEM).

Contrary to classical biotechnological approaches, in which the fluxes in one or the other pathway are favored or disfavored by overexpressing or deleting enzymes, respectively, arresting the GEM drastically reduces the demand for the building blocks of protein and RNA synthesis. Surprisingly, blocking gene expression at the GEM level leads to a reorientation of incoming nutrient fluxes towards the production of the molecule of interest.

The inventors thus designed a new *Escherichia coli* strain in which the expression of the rpoBC operon, encoding the ββ'-subunits of RNA polymerase, is put under the control of an inducible promoter. This allows the concentration of RNA polymerase to be externally set to any desired level, and thus the expression of all genes of the bacterium to be influenced.

When using a β-D-1-thiogalactopyranoside (IPTG)-dependent promoter, the inventors demonstrated that, by decreasing the IPTG concentration in the culture medium, growth can be tuned down from the rate of wild-type bacteria to a low residual rate sustained by RNA polymerases present before the start of the experiment. Moreover, the perturbation is reversible in the sense that adding IPTG to a growth-arrested culture relaunches biomass production.

Interestingly, enzymes present at the time of growth arrest and the pathways involved in the synthesis and secretion of the molecule of interest remain functional, even more so when the synthesis of these enzymes is directly or indirectly under the control of a different RNA polymerase that does not involve the ββ' subunits under the control of an inducible promoter, such as the T7 RNA polymerase.

Accordingly, the inventors created non-growing cells with a functional metabolism in which substrates supplied in the medium are utilized for the synthesis of the molecules of interest rather than biomass.

The reversibility of the blocking of RNA polymerase expression is a major advantage, since it allows alternating growth and production phases.

The method according to the invention is widely applicable to the production in bacteria of any molecule of interest, such as metabolites, peptides or recombinant proteins.

The method according to the invention has very few side-effects on the global physiology of the cell, since it does not interfere with the functioning of specific pathways and does not impose a nutrient stress possibly detrimental for the productive capacities of the cell.

Moreover, since growth arrest may be controlled by an externally-supplied inducer molecule, growth arrest is easily reversible by simply changing the composition of the growth medium. The method according to the invention is thus easy to implement.

Furthermore, the method of the invention enables a more efficient utilization of cellular biomass for the production of a molecule of interest over a longer time-period than conventional methods.

The present invention also allows improving the yield of production of the molecule of interest.

The present method also represents a gain in time since the repeated cycles of biomass production and production of the desired metabolite, peptide or recombinant protein eliminate the need to start a new culture for each production cycle.

The present invention thus concerns a method for producing at least one metabolite, peptide or recombinant protein of interest comprising the steps consisting in:
a) culturing bacteria comprising:
 (i) a gene encoding said recombinant protein or at least one gene encoding an enzyme involved in the production of said peptide or metabolite, and
 (ii) genes encoding the ββ' subunits of a bacterial RNA polymerase operably linked to an inducible promoter, in a first culture medium inducing the expression of the genes encoding said ββ' subunits, thereby inducing bacterial growth;
b) culturing said bacteria in a second culture medium inhibiting the expression of the genes encoding said ββ' subunits, and producing said metabolite, peptide, or recombinant protein while inhibiting bacterial growth;
c) optionally iterating steps a) and b) successively; and
d) optionally recovering said metabolite, peptide or recombinant protein produced by said bacteria.

The present invention also relates to the use of a bacterium comprising:
(i) a gene encoding a recombinant protein of interest or at least one gene encoding an enzyme involved in the production of a peptide or metabolite of interest, and
(ii) genes encoding the ββ' subunits of an RNA polymerase operably linked to an inducible promoter,
for producing said metabolite, peptide or recombinant protein of interest.

DETAILED DESCRIPTION OF THE INVENTION

RNA Polymerase

In the context of the invention, the term "RNA polymerase" or "RNAP" refers to an enzyme that produces RNA from DNA. Preferably, the RNA polymerase used in the context of the invention is a bacterial RNA polymerase.

As known by the skilled person, in bacteria, the core RNA polymerase enzyme is generally composed of five subunits: β, β', α', α" and ω, whereby the last subunit, ω, can often be removed without adverse effects.

The β' subunit is the largest subunit. It contains part of the active center responsible for RNA synthesis and contains some of the determinants for non-sequence-specific interactions with DNA and nascent RNA.

The β subunit is the second-largest subunit. It contains the rest of the active center responsible for RNA synthesis and contains the rest of the determinants for non-sequence-specific interactions with DNA and nascent RNA.

The β subunit and the β' subunit are the catalytic subunits of the RNA polymerase.

The α subunit is the third-largest subunit and is present in two copies per molecule of RNAP, $\alpha^I$ and $\alpha^{II}$, also referred as $\alpha_2$. Each α subunit contains two domains: αNTD (N-Terminal domain) and αCTD (C-terminal domain). αNTD contains determinants for assembly of RNAP. αCTD contains determinants for interaction with promoter DNA, making non-sequence-non-specific interactions at most promoters and sequence-specific interactions at upstream-element-containing promoters, and contains determinants for interactions with regulatory factors.

The ω subunit is the smallest subunit. It facilitates assembly of RNAP and stabilizes assembled RNAP.

In order to bind promoters, RNAP core associates with the transcription initiation sigma factor (σ) to form RNA polymerase holoenzyme. σ reduces the affinity of RNAP for nonspecific DNA while increasing specificity for promoters, allowing transcription to initiate at correct sites.

The complete holoenzyme therefore usually comprises 6 subunits: β'β $\alpha^I$ and $\alpha^{II}$ωσ.

Bacteria contain a single RNA polymerase.

The core RNA polymerase of *E. coli* has the composition $\alpha_2\beta\beta'$.

In *Escherichia coli*, the β' subunit is encoded by the rpoC gene, the β subunit is encoded by the rpoB gene, the α subunit is encoded by the rpoA gene and the ω subunit is encoded by the rpoZ gene. The major σ subunit of *E. coli* is encoded by the rpoD gene.

As the α subunit is produced in excess during growth, the amount of the ββ' subunits is the limiting factor for the production of the core enzyme.

Genes Encoding the β and β' Subunits of a Bacterial RNA Polymerase

The β and β' subunits of a bacterial RNA polymerase are encoded by at least two different genes. Said at least two genes may or may not be included in the same operon.

By "genes encoding the ββ' subunits of a bacterial RNA polymerase", it is meant herein at least one gene encoding the β subunit of a bacterial RNA polymerase and at least one gene encoding the β' subunit of said bacterial RNA polymerase.

In *E. coli*, the β and β' subunits are encoded by two genes included in the same operon, henceforth called "the rpoBC operon". The rpoBC operon comprises three transcriptional units. The first transcriptional unit comprises the rplK and rplA genes. The second transcriptional unit comprises the rplJ and rplL genes. These first and second units encode ribosomal proteins. The third unit comprises the rpoB and rpoC genes encoding the β and β' subunits, respectively. A terminator is present downstream of the rpoC gene. A transcription attenuator is present between the rplL gene and the rpoB gene.

The sequence of the *E. coli* rpoB gene is typically as set forth in sequence SEQ ID NO: 1 (EcoCyc database access number EG10894, as available on Jun. 9, 2013).

The sequence of the *E. coli* rpoC gene is typically as set forth in sequence SEQ ID NO: 2 (EcoCyc database access number EG10895, as available on Jun. 9, 2013).

In the present invention, the natural promoter of the at least one gene encoding the β subunit of a RNA polymerase and the natural promoter of the at least one gene encoding the β' subunit of a RNA polymerase are each replaced by an inducible promoter.

The genes encoding the β and β' subunits may share the same natural promoter, for example when said genes are comprised in an operon.

By "natural promoter", it is meant herein the native endogenous promoter.

By the expression "the natural promoter of a gene is replaced by an inducible promoter", it is meant herein that the natural promoter is not able anymore to activate transcription of said gene.

The natural promoter is not able anymore to activate transcription of the gene encoding the β subunit and/or of the gene encoding the β' subunit because of a total or partial deletion of said natural promoter and/or an insertion of a DNA sequence into the sequence of the natural promoter and/or the insertion of a transcription terminator upstream of the gene encoding the β subunit and/or of the gene encoding the β' subunit.

In a preferred embodiment in E. coli, the transcription of the rpoBC genes is completely isolated from the upstream ribosomal proteins by introducing a transcriptional terminator sequence between the rplL gene and the inducible promoter. The transcription of rpoBC genes by the native promoters located upstream of the rpoB gene is thus stopped.

By "rpoBC genes", it is meant herein the rpoB gene and the rpoC gene of the rpoBC operon.

The transcriptional terminator is preferably a strong transcriptional terminator, for example rrnBt1 or a synthetic terminator with a desired termination efficiency that can be constructed according to known rules for estimating termination efficiencies of simple terminators (Cambray et al. (2013), Nucleic Acids Res., doi: 10.1093/nar/gkt163, in press).

By "strong transcriptional terminator" is meant herein a terminator with a termination efficiency of at least 95%, preferably at least 96%, more preferably at least 98%. Termination efficiency may be measured as the percent reduction of expression of a reporter gene when the terminator is inserted at an appropriate location between the transcription start site and the translation start site of the reporter gene, as well known by the skilled person.

The control of the inducible promoter enables controlling the activity or concentration of the RNA polymerase, and thus controlling bacterial growth continuously between zero and the maximal growth rate supported by a given carbon source.

Inducible Promoter

The genes encoding the ββ' subunits of a bacterial RNA polymerase are operably linked to an inducible promoter.

The at least one gene encoding the β subunit and the at least one gene encoding the β' subunit are thus each operably linked to an inducible promoter.

The at least one gene encoding the β subunit and the at least one gene encoding the β' subunit may be operably linked to the same inducible promoter.

The genes encoding the ββ' subunits may be included in the same operon and be operably linked to the same inducible promoter.

In a preferred embodiment, the genes encoding the ββ' subunits of a bacterial RNA polymerase are the rpoBC genes of the rpoBC operon.

In the context of the invention, the expression "operably linked" refers to a linkage of elements (nucleic acid or protein or peptide) in a functional relationship. An element is "operably linked" when it is placed into a functional relationship with another element. For instance, a promoter or enhancer is operably linked to a coding sequence if it affects the transcription of the coding sequence. Operably linked means that the elements being linked are typically contiguous and, where necessary to join two protein coding regions, contiguous and in reading frame.

In the context of the invention, the term "promoter" refers to a nucleotide sequence that allows the binding of RNA polymerase to the DNA template in a manner such that mRNA production initiates for the downstream gene. Promoters can be typically divided into constitutive and inducible promoters.

As used herein, an "inducible promoter" is a promoter whose activity is induced by the presence or absence of biotic or abiotic factors. The activity of such promoters can be triggered by either chemical or physical factors. Chemically-regulated promoters include promoters whose transcriptional activity is regulated by the presence or absence of alcohol, tetracycline, steroids, metal and other compounds. Physically-regulated promoters include promoters whose transcriptional activity is regulated by the presence or absence of light and low or high temperatures.

Chemically-regulated promoters are well-known by the skilled person and are for example described in Terpe (2006), Appl. Microbiol. Biotechnol. 72:211-222. Examples of chemically-regulated promoters include the isopropyl β-D-1-thiogalactopyranoside (IPTG)-dependent lac promoter, the anhydrotetracycline-dependent tet promoter or the L-arabinose-dependent araBAD promoter.

Physically-regulated promoters are well-known by the skilled person and are for example described in Terpe (2006), Appl. Microbiol. Biotechnol. 72:211-222, Milias-Argeitis et al. (2011), Nat. Biotechnol. 29:1114-1116 and Levskaya et al. (2005), Nature 438:441-442. Examples of physically-regulated promoters include the temperature-dependent $p_L$ promoter, the light-responsive Phy/PIF system in yeast, or the fusion of the phytochrome Cph1 from Synechocystis PCC6803 to the E. coli histidine kinase EnvZ.

As used herein, the term "isopropyl β-D-1-thiogalactopyranoside-dependent promoter", "IPTG-dependent promoter" and "IPTG-inducible promoter" are synonymous.

Non-limiting examples of inducible promoters include the lac promoter, the/acUV5 promoter, the tac promoter, the trc promoter, the T5 promoter, the T7 promoter, the T7-lac promoter, the araBAD promoter, the rha promoter or the tet promoter.

The inducible promoter used as an example in the context of the invention is an isopropyl β-D-1-thiogalactopyranoside (IPTG)-dependent promoter.

IPTG-dependent promoters are well-known by the skilled person.

An IPTG-dependent promoter is for example the lacUV5 promoter, the tac promoter, the trc promoter, the T5-lac promoter, or the T7-lac promoter.

A preferred IPTG-dependent promoter is the T5 promoter under lac operator control, for example a T5 promoter with two embedded consecutive copies of the lac operator, as described in Lutz and Bujard (1997), Nucleic Acids Res. 25:1203-1210.

When the genes encoding the ββ' subunits of a bacterial RNA polymerase are operably linked to an IPTG-inducible promoter, it is preferred that the bacteria comprise at least one extra copy of the lacI gene, in order to reduce the probability of mutations that inactivate LacI and thus relieve repression.

The lacI gene encodes the Lac repressor responsible for the transcription inhibition in the absence of IPTG. Typically, the sequence of the lacI gene is as set forth in sequence SEQ ID NO: 3 (EcoCyc database accession number EG10525, as available on Jun. 9, 2013).

Said at least two copies of the lacI gene are preferably placed under the control of a strong promoter.

By "strong promoter" is meant herein a promoter whose strength is at least 10% of that of a rrn promoter. The rrn promoters are indeed known to be the strongest promoters in bacterial cells (Liang et al. (1999), *J. Mol. Biol.* 292:19-37).

Said at least two copies of the lacI gene may be integrated into the chromosome, preferably at different and distant loci, or they may be provided on a plasmid.

The plasmid carrying at least one copy of the lacI gene may have a replication origin allowing the plasmid to be present in a quantity of at least 10 copies in a cell, preferably at least 15 copies in a cell, more preferably at least 20 copies in a cell.

The plasmid carrying at least one copy of the lacI gene should also carry a selection marker, such as an antibiotic resistance gene. This allows selection of the bacteria containing the plasmid with said at least one copy of the lacI gene, and thus avoids loss of the plasmid.

Bacteria

Bacteria that may be used in the context of the present invention have preferably only one copy of the gene encoding the β subunit of the RNA polymerase and one copy of the gene encoding the β' subunit of the RNA polymerase.

The RNA polymerase of bacteria and the genes encoding their β and β' subunits are well known by the skilled person and these genes are conserved in different bacterial species in terms of their primary sequence, ternary structure and function (see for example Borukhov et Nudler, Trends in Microbiology, vol. 16, no. 3, 126-134, 2008).

Non-limiting examples of bacteria that may be used in the context of the present invention include the following, frequently-used species for the production of metabolites, peptides and recombinant proteins: *Escherichia coli, Bacillus subtilis, Bacillus thuringiensis, Lactobacillus fermentum, Synechocystis* sp. PCC 6803, *Corynebacterium glutanicum, Deinococcus radiodurans* and their combinations.

In a preferred embodiment, bacteria used in the present invention are *Escherichia coli* bacteria.

The bacteria according to the invention may be obtained by integration into the chromosome of starting bacteria of a cloning cassette, comprising an inducible promoter as defined in the section "Inducible promoter" above, that controls the expression of the genes encoding the ββ' subunits of a RNA polymerase.

In the case of *E. coli*, the bacteria used according to the invention comprise an rpoBC operon encoding the ββ' subunits of a RNA polymerase, the rpoBC genes being operably linked to an inducible promoter.

In the case of *E. coli*, the cloning cassette is preferably integrated into the region comprised between the rplL gene and the rpoB gene.

The starting bacteria may be *E. coli* bacteria, for example *E. coli* bacteria from a wild-type strain or from a mutated and/or recombinant strain.

In a preferred embodiment, the starting bacteria are *E. coli* bacteria from a wild-type strain.

In a more preferred embodiment, the starting bacteria are bacteria from the *E. coli* K12 BW25113 strain, *E. coli* K12 MG1655 strain, or *E. coli* BL21 strain.

The integration of the cloning cassette into the chromosome of starting bacteria can be achieved by genome engineering techniques known to the skilled person. Examples of such genome engineering techniques are homologous recombination, assembly by PCR or cloning by restriction and ligation.

The cloning cassette may also comprise a terminator sequence upstream the inducible promoter and/or a selection cassette.

In the case of *E. coli*, the terminator sequence stops transcription of the promoters located upstream of the rpoB gene. The terminator sequence is for example a strong transcriptional terminator, such as the rrnBt1 terminator.

The cloning cassette may also comprise a selection cassette encoding a selection marker, such as an antibiotic resistance protein, to allow selecting the bacteria having integrated the inducible promoter.

An example of antibiotic resistance protein is a streptomycin resistance protein, a kanamycin resistance protein, a bleomycin resistance protein, an ampicillin resistance protein, or a tetracycline resistance protein. The selection cassette is for example a streptomycin-resistance (spcR) cassette comprising the spcR gene and a promoter for the transcription of said spcR gene.

An example of cloning cassette that may be used is a cassette comprising or consisting of the sequence SEQ ID NO: 4 or sequence SEQ ID NO: 7.

As shown in FIG. 1, sequences SEQ ID NO: 4 and SEQ ID NO: 7 comprise the rrnBt1 terminator sequence, the spcR selection cassette, two lac operator sequences, the T5 inducible promoter and two homologous sequences.

The bacteria used according to the present invention may be obtained by integration of sequence SEQ ID NO: 4 or sequence SEQ ID NO: 7 into their chromosome. Preferred *Escherichia coli* bacteria for use according to the invention are bacteria obtained by integration of sequence SEQ ID NO: 4 or sequence SEQ ID NO: 7 into the chromosome of *E. coli* K12 BW25113 strain, and preferably also by integration of at least two copies of the lacI gene.

For example, bacteria *Escherichia coli* for use according to the invention are bacteria obtained by integration of sequence SEQ ID NO: 4 or sequence SEQ ID NO: 7 into the chromosome of the *E. coli* K12 BW25113 strain and integration of two copies of the lacI gene in the place of the galK gene and the intS gene. The modified chromosome of such bacteria is shown in FIG. 2. Such bacteria are for example *E. coli* bacteria from strain IJ40.

The sequence of the lacI gene inserted in the galK gene is shown in sequence SEQ ID NO: 5.

The sequence of the lacI gene inserted in the intS gene is shown in sequence SEQ ID NO: 6.

Metabolites, Peptides and Recombinant Proteins

The method according to the invention may be used for the production of at least one recombinant protein, peptide or metabolite.

Any recombinant protein, peptide or metabolite of interest may be produced, such as a recombinant protein, peptide or metabolite useful in the food or feed industry, in the pharmaceutical industry, in the cosmetic industry, in the agro industry, in the petro-chemical industry, in the environment including bioremediation and biodegradation, in research, etc.

Non-limiting examples of recombinant proteins are enzymes, pharmaceutical compounds such as inhibitors or activators, flavours, probiotic compounds, substrates, hormones or vaccines.

Non-limiting examples of peptides are certain classes of antibiotics, such as bacteriocins.

Non-limiting examples of metabolites are alcohols, such as glycerol and ethanol; amino acids, such as glutamic acid and aspartic acid; nucleotides, such as 5' guanylic acid; antioxidants, such as isoascorbic acid; organic acids, such as acetic acid and lactic acid; certain classes of antibiotics, such as kanamycin and ampicillin; and vitamins, such as vitamin B2.

A metabolite is produced by the enzymatic catalysis of at least one substrate by at least one enzyme, for example one, two, three or more enzymes.

For example, the production of glycerol from dihydroxy-acetone-phosphate involves the enzymes glycerol-3-P dehydrogenase and the glycerol-3-P phosphatase.

The bacteria used according to the invention thus also comprise a gene encoding a recombinant protein of interest or at least one gene encoding an enzyme involved in the production of a peptide or metabolite of interest. The gene encoding said recombinant protein or the at least one gene encoding an enzyme involved in the production of said peptide or metabolite may be transcribed by a second RNA polymerase, having a catalytic subunit or catalytic subunits that are different from the $\beta\beta'$ subunits of the RNA polymerase operably linked to the inducible promoter.

Said second RNA polymerase is, for example, the bacteriophage T7 polymerase or polymerases from other bacteriophages. The gene or genes encoding said second RNA polymerase may be integrated into the chromosome or they may be provided by a plasmid.

Said gene encoding the recombinant protein of interest and said at least one gene encoding an enzyme involved in the production of a peptide or metabolite of interest may be integrated into the chromosome of the bacteria or provided by a plasmid. Said plasmid comprises said gene encoding the recombinant protein of interest or said at least one gene encoding an enzyme involved in the production of a peptide or metabolite of interest, the corresponding promoter and terminator, and preferably a selection cassette wherein the selection marker is identical or different from the selection marker possibly used in the cloning cassette comprising the inducible promoter.

The promoter of said genes may be a constitutive promoter such as the pL and pRM promoters of phage $\lambda$ or the $\beta$-lactamase promoter of plasmid pBR322 (see for example Liang et al. (1999), *J. Mol. Biol.* 292:19-37). The promoter of said genes may also be an inducible promoter such of the isopropyl $\beta$-D-1-thiogalactopyranoside (IPTG)-dependent lac promoter, the anhydrotetracycline-dependent tet promoter, or the L-arabinose-dependent araBAD promoter (see for example Terpe (2006), *Appl. Microbiol. Biotechnol.* 72:211-222).

Method of Production

The present invention relates to a method for producing at least one metabolite, peptide or recombinant protein of interest in bacteria.

In some embodiments, the production of at least two or at least three peptide(s), metabolite(s) and/or recombinant protein(s) of interest is also contemplated.

The method of production comprises several steps of culture of the bacteria.

As used herein, the terms "culture" or "culturing", when referring to bacteria culture itself or the process of culturing, can be used interchangeably to mean that a bacterium is maintained under conditions suitable for survival. Cultured bacteria are allowed to survive, and culturing can result in cell growth or division. The term does not imply that all bacteria in the culture survive or grow or divide, as some may naturally senesce, etc. Bacteria are typically cultured in a medium, which can be changed during the course of the culture.

The skilled person knows how to define the optimal culture conditions for given bacteria, in particularly the composition of the medium, the mode of culture, the temperature, the pH, etc.

The terms "medium" or "culture solution" refers to a medium appropriate for the culture of bacteria. A medium is typically an isotonic solution, and can be liquid, gelatinous, or semi-solid. The media, as used herein, can include the components for nutritional, chemical, and structural support necessary for culturing bacteria.

As used herein, "fresh medium" refers to the initial medium that has not been in contact with the bacteria.

As used herein, "culture medium" refers to the initial medium that has possibly been in contact with the bacteria.

Typically, the medium comprises at least one source of carbon, at least one source of nitrogen, at least one source of sulphur, at least one source of phosphorus, at least one source of potassium, and at least one source of minerals.

The medium may be supplemented with at least one source of vitamins.

The source of nitrogen is, for example, selected from the group of compounds consisting of ammonium chloride, ammonium sulphate, ammonium hydroxide, di-ammonium phosphate, ammonia, urea, glutamine and a combination thereof.

The source of sulphur is, for example, selected from the group of compounds consisting of ammonium sulphate, magnesium sulphate, sulphuric acid and a combination thereof.

The source of phosphorus is, for example, selected from the group of compounds consisting of disodium phosphate, phosphoric acid, potassium phosphate, di-ammonium phosphate, mono-ammonium phosphate and a combination thereof.

The source of potassium is, for example, selected from the group of compounds consisting of potassium phosphate, potassium chloride, potassium sulphate and their combinations.

The source of mineral salts may particularly provide magnesium, calcium, sodium, iron, zinc, cobalt, copper, molybdenum, selenium, manganese, borium or their combinations.

The source of vitamins is, for example, selected from the group consisting of yeast hydrolysate, pure vitamin solution, a mixture of pure vitamins and a combination thereof.

Typical media that may be used are minimal media, preferably supplemented with the required nutriments, or rich media.

Examples of medium that may be used for the culture of bacteria are M9 minimal medium supplemented with 0.4% of glucose, M9 minimal medium supplemented with 0.4% of glucose and casomino acids, or lysogeny broth (LB) medium.

M9 minimal medium has a standard composition, as for example described in *Cold Spring Harbor Protocols* (doi: 10.1101/pdb.rec12295, 2010). This minimal medium can be supplemented with vitamins and mineral salts as detailed above.

The composition of the M9 minimal medium used according to the invention is as follows: disodium phosphate: 6.8 g/l, potassium phosphate: 3 g/l, sodium chloride: 0.5 g/l, ammonium chloride: 1 g/l or 2 g/l, magnesium sulphate: 0.24 g/l, calcium chloride: 0.011 g/l.

The culture of the bacteria is preferably performed in a fermenter suitable for the production of bacteria.

The culture of the bacteria may be a batch, a fed-batch, a continuous culture or their combinations.

By the term "batch" is meant herein a culture in a fermenter carried out in the initial medium and wherein there is no entrance of fresh medium and no removal of the culture medium in the fermenter.

By the expression "semi-continuous culture", "culture in semi-continuous mode" or "fed-batch" is meant herein a culture in a fermenter which is progressively fed by the medium, no volume of medium being removed during the culture. In such a method, the volume of culture is variable in the fermenter.

By the expression "continuous culture" or "culture in a continuous mode" is meant herein a culture in a fermenter during which the fermenter is fed with fresh medium and in which part of the culture medium is removed, so that the volume of culture in the fermenter is variable or constant.

The temperature of the culture medium may be comprised between 0° C. and 100° C., preferably between 20° C. and 45° C., more preferably between 30° C. and 40° C., and most preferably at 37° C.

Temperature of the culture medium may vary during the culture of bacteria.

The temperature of the culture medium may be measured during the culture.

In a preferred embodiment, the temperature is maintained at a given temperature during the culture, for example 37° C.

For that purpose, the fermenter may comprise means for measuring and/or controlling temperature in the culture medium.

The pH of the culture medium may be comprised between pH 5 and pH 9, preferably between pH 7 and pH 8, more preferably at pH 7.5.

pH may vary during the culture of bacteria.

pH of the culture medium may be measured during the culture.

In a preferred embodiment, pH of the culture medium is maintained at a given pH during the culture, for example at pH 7.5.

For that purpose, the fermenter may comprise means for controlling pH.

A buffer such as phosphate buffer, in particular $K_xH_yPO_4$ may be used to control the pH of the culture medium.

Cultures are preferably shaken or stirred, continuously or not.

Step a) of the Method of Production

The method of production of the invention comprises a step a) of culturing bacteria comprising:
(i) a gene encoding said recombinant protein or at least one gene encoding an enzyme involved in the production of said peptide or metabolite, as defined in the section "Metabolites, peptides, and recombinant proteins" hereabove, and
(ii) genes encoding the ββ' subunits of a bacterial RNA polymerase, as defined in the section "Genes encoding the ββ' subunits of RNA polymerase" hereabove operably linked to an inducible promoter, as defined in the section "Inducible promoter" hereabove,
in a first culture medium inducing the expression of the genes encoding the ββ' subunits of RNA polymerase, thereby inducing bacterial growth.

Bacteria are as defined above in the section "Bacteria".

The aim of this first step of culture is therefore to induce the expression of the genes encoding the ββ' subunits of RNA polymerase in order to induce bacterial growth.

By "inducing the expression of the genes encoding the ββ' subunits of RNA polymerase" is meant enabling the transcription of the genes into mRNA encoding the ββ' subunits of the RNA polymerase as defined in the section "Genes encoding the ββ' subunits of RNA polymerase" hereabove, and the translation of this mRNA into the ββ' subunits.

Such an induction of the expression of the genes encoding the ββ' subunits of RNA polymerase is obtained by activating the inducible promoter operably linked to the genes encoding the ββ' subunits of RNA polymerase or by inhibiting the repression of the inducible promoter operably linked to the genes encoding the ββ' subunits of RNA polymerase.

Techniques to induce the expression of the genes encoding the ββ' subunits of RNA polymerase with the first culture medium depend on the type of inducible promoter operably linked to the genes. Such techniques are well-known to the skilled person.

In a preferred embodiment, said genes encoding the ββ' subunits of RNA polymerase are the ropBC genes of the rpoBC operon.

In a preferred embodiment, said inducible promoter is an IPTG-dependent promoter.

When the inducible promoter is an IPTG-dependent promoter, expression of the genes encoding the ββ' subunits of RNA polymerase can be induced in a medium comprising IPTG.

For example, the first culture medium of step a) comprises IPTG.

The concentration of IPTG in the first medium may be comprised between 0.1 mM and 1 mM, preferably between 0.3 mM and 0.7 mM, more preferably 0.5 mM.

A preferred first culture medium of step a) comprises M9 minimal medium supplemented with 0.4% glucose and 0.5 mM IPTG.

The induction of the promoter by IPTG may be tested by means of quantification of the rpoBC mRNA, using techniques well-known by the skilled person, or by means of quantification of the β and β' subunits, using techniques also well-known by the skilled person.

The induction of bacterial growth may be monitored by measuring the population density.

"Population density" refers herein to the number of bacteria cells in a given volume.

The present invention particularly relates to a method as defined above, wherein the bacteria are cultured in step a) until a desired population density is reached.

The bacterial growth usually comprises at least the first two following phases:
a lag phase, wherein there is no growth,
an exponential phase, wherein the growth increases exponentially,
a stationary phase, wherein there is no more growth, and
a decline phase, wherein there is no growth and cells progressively die.

The desired population density is reached in step a) preferably at the beginning and/or in the middle of the exponential phase, i.e. when a sufficient amount of nutrients for the production of said metabolite, peptide or protein remains in the medium.

Population density may be measured by any suitable method well known by the skilled person.

Population density may be measured in a sample removed from the culture medium that has been shaken or stirred to have a homogenous cell distribution.

The sample is thus in the form of a cell suspension.

Population density may be measured by direct methods, such as by counting the number of cells by volume unit of a cell suspension, for example by using a Malassez counting chamber, by flow cytometry, by counting the number of colonies formed in agar plates after serial dilutions of the sample.

Population density may also be measured by indirect methods, such as turbidity measurement.

Turbidity measurement may be an optical density (OD) measurement, also called absorbance measurement.

Several wavelengths may be used to measure turbidity. A preferred wavelength is 600 nm. The term "$OD_{600}$" is the optical density of a sample measured at a wavelength of 600 nm. Typically, OD is measured in a spectrophotometer or in a microplate reader.

The present invention particularly relates to a method as defined above, wherein the bacteria are cultured in step a) until a population density comprised between 0.1 and 100 $OD_{600}$ is reached, preferably between 0.3 and 50 $OD_{600}$, more preferably between 0.5 and 1 $OD_{600}$ for a glucose concentration of 0.4%.

The present invention particularly relates to a method as defined above, wherein the bacteria are cultured in step a) until the population density corresponds to that of a bacterial culture at the beginning or in the middle of the exponential phase.

Step b) of the Method of Production

The method of production of the invention comprises a step b) of culturing said bacteria in a second culture medium inhibiting the expression of the genes encoding said ββ' subunits and producing said metabolite, peptide or recombinant protein while inhibiting bacterial growth.

The aim of this second step of culture is therefore to inhibit the expression of the genes encoding the ββ' subunits of RNA polymerase in order to inhibit bacterial growth.

By "inhibiting the expression of the genes encoding the ββ' subunits of RNA polymerase" is meant inhibiting or stopping the transcription of the said genes into mRNA encoding the ββ' subunits of the RNA polymerase as defined in the section "Genes encoding the ββ' subunits of RNA polymerase" hereabove, and the translation of this mRNA into the ββ' subunits.

Such an inhibition of the expression of the genes encoding the ββ' subunits of RNA polymerase is obtained by inactivating the inducible promoter operably linked to the genes encoding the ββ' subunits of RNA polymerase or by inducing the repression of the inducible promoter operably linked to the genes encoding the ββ' subunits of RNA polymerase.

Techniques to inhibit the expression of the genes encoding the ββ' subunits of RNA polymerase with the second culture medium depend on the type of inducible promoter operably linked to the genes encoding the ββ' subunits of RNA polymerase. Such techniques are well-known to the skilled person.

The second culture medium may be equal to the first culture medium, for example if the inducible promoter used is a light-sensitive promoter or a temperature-sensitive promoter.

When the inducible promoter is an IPTG-dependent promoter, expression of the genes encoding the ββ' subunits of RNA polymerase can be inhibited in a medium free of IPTG.

For example, the second culture medium of step b) is free of IPTG.

The second culture medium of step b) preferably comprises M9 minimal medium supplemented with 0.4% glucose and is free of IPTG.

The present invention particularly relates to a method as defined above wherein the first culture medium of step a) comprises IPTG and the second culture medium of step b) is free of IPTG.

The present invention particularly relates to a method as defined above, wherein said first culture medium of step a) comprises M9 minimal medium supplemented with 0.4% glucose and 0.5 mM IPTG and said second culture medium of step b) comprises M9 minimal medium supplemented with 0.4% glucose and is free of IPTG.

If the inducible promoter is a light-sensitive promoter or a temperature-sensitive promoter, the growth medium may not be changed between steps a) and b), but the illumination or temperature of the culture is modified.

The production of the recombinant protein, peptide or metabolite of interest may be measured during step b) and/or at the end of step b).

In a preferred embodiment, the present invention thus relates to a method as defined above further comprising measuring the metabolic activity of the cultured bacteria during step b).

By "metabolic activity", it is meant herein the metabolic activity linked to the production of the recombinant protein, peptide or metabolite of interest and/or any other cellular process involving the uptake and assimilation of extracellular substrates.

For example, the metabolic activity may be a measure of the concentration or the rate of change of the concentration of said metabolite, peptide or recombinant protein of interest itself; a measure of the activity or the rate of change of the activity of said metabolite, peptide or recombinant protein of interest; a measure of the concentration and/or activity or the rate of change of the concentration and/or activity of at least one indirect product; or their combinations.

Said indirect product may be an enzyme involved in the production of the peptide or metabolite, an intermediary product, a by-product or a substrate, involved in the production of said metabolite, peptide or recombinant protein of interest.

The skilled person knows methods suitable for measuring the concentration and/or activity, or the rate of change of the concentration and/or activity, of the above-mentioned compounds.

Non-limiting examples of metabolic activity that may be measured according to the present invention are the luminescence level or the rate of change of the luminescence level when the recombinant protein is a luminescent protein, such as luciferase; the fluorescence level or the rate of change of the fluorescence level when the recombinant protein is a fluorescent protein such as the GFP (Green Fluorescent Protein); glycerol concentration or rate of change of glycerol concentration; glucose concentration or rate of change of glucose concentration; concentration or activity or rate of change of concentration or activity of glycerol-3-P dehydrogenase and/or of glycerol-3-P phosphatase, when the metabolite is glycerol.

Step c) of the Method of Production

The present invention also relates to a method as defined above, comprising a step c), wherein steps a) and b) are iterated successively.

For example, steps a) and b) may be iterated once, twice, three times or more.

Steps a) and b) may be iterated until the end of exponential growth of the bacterial culture is reached.

The present invention particularly relates to a method as defined above, wherein step c) is carried out when the metabolic activity measured during step b) decreases.

Step d) of the Method of Production

The method according to the invention may comprise a step d) of recovering said metabolite, peptide or recombinant protein produced by said bacteria.

The step of recovering will depend on the metabolite, peptide or recombinant protein produced by said bacteria, particularly if said metabolite, peptide or recombinant protein is expressed in the bacteria or is excreted into the culture medium.

When the metabolite, peptide or recombinant protein is expressed in the bacteria, the step of recovering may comprise one or several steps of washing the bacteria, lysing the bacteria, and purifying the desired product.

When the metabolite, peptide or recombinant protein is excreted into the culture medium, the step of recovering may comprise one or several steps of removing the metabolite, peptide or recombinant protein from the medium and purifying the said metabolite, peptide or recombinant protein.

Such techniques are well known to the skilled person.

The step of recovering may also consist in harvesting and washing bacteria, and eventually lysing and/or drying the bacteria.

Step a') of the Method of Production

The present invention relates to a method as defined above, further comprising a step a') between steps a) and b) consisting in harvesting and optionally washing the bacteria cultured in step a) and transferring them into the second culture medium of step b).

The harvesting step comprises, for example, the centrifugation of the first culture medium comprising the bacteria, the supernatant being then removed.

The harvesting step is preferably followed by at least one washing step, preferably in the same medium as the second medium used in step b).

The optionally washed bacteria are then transferred to the second culture medium which has not been in contact with bacteria.

If steps a) and b) are iterated, the bacteria cultured in step b) may similarly be harvested, optionally washed, and transferred to a fresh first medium of step a).

Step Pre-a) of the Method of Production

The present invention also relates to a method as defined above, further comprising a step pre-a) before step a) consisting in providing bacteria comprising:
(i) a gene encoding said recombinant protein or at least one gene encoding an enzyme involved in the production of said peptide or metabolite, and
(ii) genes encoding the ββ' subunits of an RNA polymerase operably linked to an inducible promoter.

The step of a providing bacteria comprising:
(i) a gene encoding said recombinant protein or at least one gene encoding an enzyme involved in the production of said peptide or metabolite, and
(ii) genes encoding the ββ' subunits of an RNA polymerase operably linked to an inducible promoter,
may comprise a step of producing said bacteria, particularly using genetic engineering techniques as defined above in the section "Bacteria".

Use for Producing Metabolites, Peptides or Recombinant Proteins

In another embodiment, the present invention relates to the use of a bacterium comprising:
(i) a gene encoding a recombinant protein of interest or at least one gene encoding an enzyme involved in the production of a metabolite or peptide of interest, and
(ii) genes encoding the ββ' subunits of a RNA polymerase operably linked to an inducible promoter,
for producing said metabolite, peptide or recombinant protein of interest.

The present invention particularly relates to the use as defined above wherein bacteria are cultured in a first culture medium inducing the expression of the genes encoding the ββ' subunits of RNA polymerase, thereby inducing bacterial growth and then cultured in a second culture medium inhibiting the expression of the genes encoding the ββ' subunits of RNA polymerase and producing said metabolite, peptide or recombinant protein while inhibiting bacterial growth.

The present invention also relates to the use as defined above, wherein said inducible promoter is an IPTG-dependent promoter.

The present invention also relates to the use as defined above, wherein the first culture medium comprises IPTG and the second culture medium is free of IPTG.

The present invention also relates to the use as defined above, wherein the gene encoding said recombinant protein or said at least one gene encoding an enzyme involved in the production of said peptide or metabolite is transcribed by a second RNA polymerase having a catalytic subunit or catalytic subunits that are different from the ββ' subunits of the RNA polymerase operably linked to the inducible promoter.

The present invention also relates to the use as defined above, wherein said second RNA polymerase is the bacteriophage T7 polymerase.

Bacteria are as defined above in the section "Bacteria". In a preferred embodiment, the present invention relates to the use as defined above, wherein said bacterium is *Escherichia coli* strain IJ40.

The media are as defined above.

The density of population and metabolic activity may be monitored as defined above.

The present invention will be further illustrated by the following examples.

BRIEF DESCRIPTION OF THE FIGURES

FIG. 1: rpoBC operon in *E. coli* and cloning cassette.

A. The rpoBC operon comprises a first transcriptional unit comprising the rplK and rplA genes, a second transcriptional unit comprising the rplJ and rplL genes, and a third unit comprising the rpoB and rpoC genes encoding the β and β' subunits, respectively. A terminator (T) is present downstream of the rpoC gene. A transcription attenuator (A) is present between the rplL gene and the rpoB gene. The homologous sequences of the chromosome and the cassette are also shown (dotted).

B. The cloning cassette of sequence SEQ ID NO: 4 or sequence SEQ ID NO: 7 comprises two homologous sequences (dotted) flanking the rrnBt1 terminator sequence (T), the spcR selection cassette, two lac operator sequences and the T5 inducible promoter.

FIG. 2: Modifications of the chromosome of an *E. coli* bacterium according to the invention, such as IJ40 strain bacterium.

The chromosome was modified by integration of an inducible promoter operably linked to the rpoBC operon and the replacement of genes galK and intS by two copies of the lacI gene.

EXAMPLES

Material and Methods

Bacteria

*Escherichia coli* strain IJ40 is derived from *E. coli* K12 BW25113 strain.

Strain IJ40 was obtained from *E. coli* K12 BW25113 by integration into the chromosome of the T5 IPTG dependent-promoter in front of the rpoBC operon and two copies of the lacI gene (cf. FIG. 2). The cloning cassette comprising the T5 IPTG dependent-promoter is shown in sequence SEQ ID NO: 7. The two copies of the lacI gene have been integrated in replacement of the genes galK and intS (as shown in sequences SEQ ID NO: 5 and 6, respectively); they provide a large amount of the Lac repressor and prevent the appearance of fixed mutation.

Plasmids pSB-crp-lux plasmid comprising a transcriptional fusion of the promoter of the gene encoding the Crp transcription regulator and the luxCDABE operon is used for assessing the cellular metabolism activity after growth arrest.

pSKG plasmid, comprising two enzymes, the glycerol-3-P dehydrogenase (encoded by the gpd1 gene) and the glycerol-3-P phosphatase (encoded by the gpp2 gene) from yeast is used for the production of glycerol (Liang et al. (2011), *Appl. Microbiol. BiotechnoL*, 89:57-62).

pUA66 plasmid carrying a transcriptional fusion of the pRM promoter of phage λ, which is constitutive in non-infected *E. coli* cells (Berthoumieux et al. (2013), *Mol. Syst. Biol.* 9:634), and the gene coding for the fast-folding, stable fluorescent protein GFPmut2 (Zaslaver et al. (2006), *Nat. Methods* 3:623-628) is used to transform *Escherichia coli* IJ40 strain for the production of a recombinant fluorescent protein.

Medium

M9 minimal medium has a standard composition, as for example described in *Cold Spring Harbor Protocols* (doi: 10.1101/pdb.rec12295, 2010).

The composition of the M9 minimal medium used in the examples is as follows: disodium phosphate: 6.8 g/l, potassium phosphate: 3 g/l, sodium chloride: 0.5 g/l, ammonium chloride: 2 g/l, magnesium sulphate: 0.24 g/l, calcium chloride: 0.011 g/l.

The medium used for the bacterial growth is said M9 minimal medium supplemented with 0.4% glucose and 0.5 mM IPTG.

The medium used for inhibiting bacterial growth is said M9 minimal medium supplemented with 0.4% glucose.

Production of the Metabolite, Peptide or Recombinant Protein

The method of production of the metabolite, peptide or recombinant protein of interest comprises the following steps.

A pre-culture of strain IJ40 cells transformed with the plasmid of interest is carried out for 18 hours à 37° C. in a M9 medium supplemented with 0.4% of glucose containing 0.5 mM IPTG. At time zero, IPTG is removed from the overnight culture by centrifugation for 5 min at 4,000 g and the cells are washed with fresh M9 medium without IPTG. This operation is repeated twice and the inoculum size is adjusted to give equal optical density to all cultures. The washed cultures of equal optical density are diluted 100 fold into fresh medium supplemented with 0.4% of glucose and containing 0.5 mM IPTG to reach an initial $OD_{600}$ of 0.01.

This first step of culture is carried out at 37° C. until the density of population of 0.5 $OD_{600}$ is reached. The cells of the first step are then harvested and washed with fresh M9 medium without IPTG, before being transferred into a fresh M9 medium supplemented with 0.4% of glucose without IPTG. This second step of culture is carried out at 37° C. until after about 10 h. The cultures of the first and second steps are shaken and the absorbance at 600 nm is read every 5 minutes by an automated plate reader.

The cells of the second step may then be harvested and washed with fresh M9 medium without IPTG, before being transferred into a fresh M9 medium supplemented with 0.4% of glucose and containing 0.5 mM IPTG. The above first step and second step may then be repeated once or several times.

Results (i) Assessment of the Cellular Metabolism Activity after Growth Arrest

*Escherichia coli* IJ40 strain is transformed with the pSB-crp-iux plasmid comprising a transcriptional fusion of the promoter of the gene encoding the Crp transcription regulator, whose expression is known to vary little across growth phases (Kuhlman et al. (2007), *Proc. Natl Acad. Sci. USA* 104: 6043-6048), and the luxCDABE operon, which encodes the enzymes necessary for the production of bacterial luciferase as well as the production of the aldehyde substrate of bacterial luciferase.

The production of the transformed strain is carried out with a first step of culture in the medium with IPTG and a second step of culture in the same medium free of IPTG as described in the Material and Methods.

The metabolic activity after growth arrest of this strain manifests itself through a sustained glucose influx, leading to the maintenance of a high ATP/ADP ratio. This latter ratio can be measured using the luminescent reporter encoded by the pSB-crp-iux plasmid, since ATP is a co-factor required for luminescence production (Meighen et al. (1999), *Microbiol. Rev.* 55:123-142). In particular, a non-decreasing luminescence level per cell after growth arrest is an indicator of the maintenance of the ATP/ADP ratio. This is experimentally verified when the luminescence emitted by a population of *E. coli* cells is measured over time and divided by the optical density of the culture.

Cellular metabolism is thus active after growth arrest and the above-mentioned method can be used for the production of metabolites, peptides or recombinant protein.

(ii) Production of Glycerol in Bacteria with Improved Yield

*Escherichia coli* IJ40 strain is transformed with the pSKG plasmid (or an equivalent plasmid expressing the same functional enzymes), allowing the expression of two enzymes, glycerol-3-P dehydrogenase (encoded by the gpd1 gene) and glycerol-3-P phosphatase (encoded by the gpp2 gene) from yeast (Liang et al. (2011), *Appl. Microbiol. Biotechnol.*, 89:57-62). These enzymes convert the glycolysis intermediate dihydroxyacetone-phosphate into glycerol, thus turning the recombinant IJ40 strain into a glycerol production strain.

The production of glycerol is carried out with a first step of culture in the medium with IPTG and a second step of culture in the same medium free of IPTG, as described in the Material and Methods.

Glucose and glycerol concentrations are measured in the medium over time, by means of commercially-available kits and the yield is computed.

The transformed IJ40 strain is capable of glycerol production during growth on glucose and, more importantly, during growth arrest. Moreover, the yield of glycerol in the growth-arrested state is higher than during growth on glucose.

(iii) Production of a Recombinant Fluorescent Protein in Bacteria with Improved Yield

*Escherichia coli* IJ40 strain is transformed with a pUA66 plasmid carrying a transcriptional fusion of the pRM promoter of phage λ, which is constitutive in non-infected *E. coli* cells (Berthoumieux et al. (2013), *Mol. Syst. Biol.* 9:634), and the gene coding for the fast-folding, stable fluorescent protein GFPmut2 (Zaslaver et al. (2006), *Nat. Methods* 3:623-628). The measured fluorescence is proportional to the total quantity of GFP in the cell population. The production of the recombinant fluorescent protein is carried out with a first step of culture in the medium with IPTG and a second step of culture in the same medium free of IPTG, as described in the Material and Methods.

The fluorescence emitted by the culture and the optical density in a microplate reader are dynamically monitored.

Cells continue to emit fluorescence after growth arrest and the GFP concentration per cell, obtained by dividing the fluorescence intensity by the optical density, is larger for the growth-arrested cells than for those growing on glucose.

CONCLUSIONS

The method of the invention based on the possibly repeated arrest and restart of the GEM allows improving the production of molecules for biotechnological applications. Cellular metabolism is active after growth arrest and the method according to the invention allows improving the yield of metabolites, peptides, and recombinant proteins.

The invention claimed is:

1. A method for producing at least one metabolite, peptide, or recombinant protein of interest, said method comprising the steps consisting in:
   a) culturing bacteria comprising:
      (i) a gene encoding said recombinant protein or at least one gene encoding an enzyme involved in the production of said peptide or metabolite,
      wherein said gene is operably linked to a promoter, and
      (ii) genes encoding the ββ' subunits of a bacterial RNA polymerase operably linked to an inducible promoter,
      wherein the promoter operably linked to the genes in (i) and (ii) are not the same,
      in a first culture medium comprising an inducer of the inducible promoter operably linked to the genes of (ii) and thereby inducing the expression of the genes encoding said ββ' subunits, thereby inducing bacterial growth;
b) culturing said bacteria in a second culture medium lacking the inducer and thereby inhibiting the expression of the genes encoding said ββ' subunits and inhibiting bacterial growth while the gene encoding said recombinant protein or at least one gene encoding an enzyme involved in the production of said peptide or metabolite continues to be expressed, thereby producing said metabolite, peptide or recombinant protein;
c) optionally iterating steps a) and b) successively; and
d) optionally recovering said metabolite, peptide or recombinant protein produced by said bacteria.

2. The method according to claim 1, wherein said inducible promoter is an IPTG-dependent promoter.

3. The method according to claim 1, wherein the first culture medium of step a) comprises IPTG and the second culture medium of step b) is free of IPTG.

4. The method according claim 1, wherein the gene encoding said recombinant protein or said at least one gene encoding an enzyme involved in the production of said peptide or metabolite is transcribed by a second RNA polymerase having a catalytic subunit or catalytic subunits that are different from the sp' subunits of the RNA polymerase operably linked to the inducible promoter.

5. The method according to claim 4, where said second RNA polymerase is the bacteriophage T7 polymerase.

6. The method according to claim 1, wherein said bacteria comprise at least two copies of the lacI gene.

7. The method according to claim 1, wherein said bacteria are *Escherichia coli* bacteria.

8. The method according to claim 1, wherein said genes encoding the ββ' subunits of RNA polymerase are the rpoBC genes of the rpoBC operon.

9. The method according to claim 1, wherein the bacteria are cultured in step a) until a population density comprised from 0.1 to 100 $OD_{600}$ is reached.

10. The method according to claim 1, further comprising a step a') between steps a) and b) consisting in harvesting and optionally washing the bacteria cultured in step a) and transferring them into the second culture medium of step b).

11. The method according to claim 1, further comprising measuring the metabolic activity of the cultured bacteria during step b).

12. The method according to claim 11, wherein step c) is carried out when the metabolic activity measured during step b) decreases.

13. The method according to claim 1, wherein said first culture medium of step a) comprises M9 minimal medium supplemented with 0.4% glucose and 0.5 mM IPTG and said second culture medium of step b) comprises M9 minimal medium supplemented with 0.4% glucose and is free of IPTG.

* * * * *